United States Patent [19]

Wen et al.

[11] Patent Number: 5,027,642
[45] Date of Patent: Jul. 2, 1991

[54] METHOD OF DETECTING AND OR REMOVING TRACE AMOUNTS OF CONDENSIBLE VAPORS FROM COMPRESSED GAS

[75] Inventors: HorngYuan Wen, Brookfield; Gerhard Kasper, Downers Grove; Donell Montgomery, Chicago, all of Ill.

[73] Assignee: American Air Liquide, New York, N.Y.

[21] Appl. No.: 107,177

[22] Filed: Oct. 13, 1987

[51] Int. Cl.$^5$ ............................................. G01N 21/00
[52] U.S. Cl. ........................ 73/23.2; 73/28.01; 73/31.03; 55/82; 55/319; 55/323; 55/327; 55/DIG. 17; 55/DIG. 25; 62/85; 324/71.4; 356/336; 436/177; 436/178; 436/181
[58] Field of Search ........... 436/36, 175, 177, 181, 436/178; 55/92, 82, 319, 323, 327, DIG. 17, DIG. 25; 62/85, 195; 73/23.2, 31.03, 28.01; 324/71.4; 356/336, 337, 37

[56] References Cited

U.S. PATENT DOCUMENTS

| | | | |
|---|---|---|---|
| 1,697,344 | 1/1929 | Campbell | 73/211 |
| 3,037,421 | 6/1962 | Bigelow et al. | 88/14 |
| 3,102,192 | 8/1963 | Skala | 250/43.5 |
| 4,272,499 | 6/1981 | Cason et al. | 423/242 |
| 4,358,302 | 11/1982 | Dahneke | 55/392 |
| 4,878,510 | 11/1989 | Kasper et al. | 137/1 |

FOREIGN PATENT DOCUMENTS 330151 12/1920 Fed. Rep. of Germany ........... 47/1
794834 7/1955 United Kingdom .

OTHER PUBLICATIONS

"A Gas Filtration System for Concentrations of $10^{-5}$ Particles/cm$^3$", Kasper and Wen, Aerosol Science and Technology, 1986.
Table of Contents of "Nucleation", by Zettlemoyer (1969).

Primary Examiner—David L. Lacey
Assistant Examiner—David Redding
Attorney, Agent, or Firm—Curtis, Morris & Safford

[57] ABSTRACT

A method to detect, measure or remove trace amounts of condensible vapors in compressed gases. The concentration of droplets detected, measured or removed may be as low as part per trillion. The compressed gas comprising a carrier gas and condensible vapors is discharged through a critical orifice in order to condense the vapors in the form of homogeneous droplets. The droplets are either detected, or their concentration measured or removed from the expanded carrier gas.

20 Claims, 3 Drawing Sheets

METHOD OF DETECTING AND OR REMOVING TRACE AMOUNTS OF CONDENSIBLE VAPORS FROM COMPRESSED GAS

BACKGROUND OF THE INVENTION

The invention relates to the detection of trace amounts of condensible vapors in compressed gases, the measurement of their concentration and, further, their removal from the said compressed gases.

In many applications of gases, such as manufacture of VLSI chips, high purity gases are needed during the manufacturing process to avoid, among others, the creation of defects during the various masking steps of the process and thus enhance the manufacture output of said process as well as the reliability of the chips. There is also a need for high purity gases in the optical, aerospace and pharmaceutical industries.

Various impurities such as particles or vapors may be present in compressed gases stored in a container such as a cylinder. It is known from the article entitled "A gas filtration system for concentrations of $10^{-5}$ paticles/cm$^3$" from G. KASPER and H. Y. WEN; published in Aerosol Science and Technology 5: 167-185 (1986), to achieve "totally" particle-free process gases. Particle analysis has been also carefully studied by the same authors and the results of this study published in Proceedings—Institute of Environmental Sciences—May 6, 1987—in an article entitled "Particle Analysis in cylinder gases".

Trace quantities of condensible vapors such as hydrocarbons or fluorinated hydrocarbons in gases are commonly detected and quantified by a variety of means such as chromatography in the gas phase, IR absorption spectroscopy, mass spectrometry, total hydrocarbon detectors, etc.

However, detection limits of such techniques are about 100 ppb, while with a preconcentration step, such capabilities are about 1 ppb (part per billion). Such methods are time-consuming, especially when they comprise a pre-concentration step, costly and in some cases very costly and relatively insensitive to higher order hydrocarbons. Furthermore, such methods provide means for measuring the concentration of such vapors, with a limited accuracy but do not provide means for removing said vapors based on the same concept.

It is an object of the present invention to define a method to detect the presence of trace amounts up to part per trillion or less of condensible vapors in compressed gases.

It is a further object of the present invention to measure the concentration of trace amounts up to part per trillion or less of condensible vapors in compressed gases.

It is a further object of the present invention to remove trace amounts up to part per trillion or less of condensible vapors in compressed gases.

SUMMARY OF THE INVENTION

The method of the invention is based on the fact that the inventors were the first to recognize that condensation in expanding jets could be used to detect, quantity and/or remove condensible impurities and/or to regulate a process via the detection of aerosols formed by condensation.

According to a first embodiment, the invention relates to a method of detecting trace amounts of condensible vapors from compressed gas comprising the steps of providing a compressed gas at a high pressure, filtering said compressed gas to remove particles present in said high pressure gas, expanding said compressed gas to a low pressure through a critical orifice, detecting the presence of droplets of condensed vapors in said low pressure gas.

According to a second embodiment, the invention relates to a method of providing a measure for the concentration of condensible vapors in a gas compressed under high pressure, comprising the steps of providing a compressed gas at a high pressure, filtering said compressed gas to remove particles present in said high pressure gas, expanding said gas to a low pressure through a critical orifice, measuring the concentration of droplet concentration of condensed vapors in the expanded gas, comparing said measure to a threshold concentration.

This second embodiment thus provides a measure, for a given pressure drop, whether the initial concentration is above a given level or not. Such information is useful, for example, in certain quality control applications.

According to a third embodiment, the invention relates to a method of providing a measure for the concentration of condensible vapors in a gas compressed under high pressure, comprising the steps of providing a compressed gas at a high pressure, filtering said compressed gas to remove particles present in said high pressure gas, expanding said gas to a low pressure through a critical orifice, varying the pressure drop across the critical orifice, measuring the concentration of droplets as a function of pressure drop.

Depending on the application this third embodiment may further comprise a step of comparing the measured concentrations of droplets with a threshold concentration of droplets and a step of determining the value of the pressure drop at which the droplets concentration exceeds the threshold value. The value of the pressure drop is a measure of the purity of the gas.

According to a fourth embodiment, the invention relates to a method of removing trace amounts of condensible vapors in a compressed carrier gas stored at a high pressure, comprising the steps of providing a compressed gas at a high pressure, filtering said compressed gas to remove particles present in said high pressure gas, expanding said gas to a lower pressure through a critical orifice, the pressure drop between said first and second pressures being sufficient to cause the onset of droplets formation by said condensible vapors in the expanded carrier gas, maintaining the temperature of said expanded carrier gas at a sufficient value to avoid reevaporation of the droplets, capturing the said droplets to remove the condensed vapors from said carrier gas. The proportion of condensible vapors which are condensed by such expansion depends on the pressure drop through the critical orifice, which further determines the temperature drop of the gas.

Means for capturing the droplets are well known, i.e, filtration, absorption or the like.

Those four embodiments may further comprise a purification step before the filtering step, in order to remove a maximum of condensible vapors by conventional means such as molecular sieves refrigerated in dry ice, liquid nitrogen, or the like, before expansion. This further step may be used to determine a threshold value of particles which may be further acceptable.

DESCRIPTION OF THE METHOD STEPS

According to the invention, compressed gases are defined as comprising, among others, a carrier gas and condensible vapors. Condensible vapors are defined for the present purposes as species which will condense to form droplets upon sufficient cooling of the carrier gas, which however are present in their gaseous state before cooling and hence not as droplets. The method according to the invention thus distinguishes itself from other dectection methods for preexisting particles and specifically from methods for the detection of preexisting oil droplets in gases which require the preexistance of such droplets. An example of such methods is given in U.S. patent application Ser. No. 801.305, G. Kasper and al.

The various embodiments disclosed above aim at the detection of global amounts of condensible vapors within a "family" of such species (for example hydrocarbons) rather than individually detecting each component. A "family" is defined as a group of species with relatively simultaneous onset of condensation as observed by the method of the invention. It is thus possible to detect both condensible vapors (as defined above) and preexisting droplets in the carrier gas (as mentioned above). However, it is possible if, according to one embodiment of the invention, only condensible vapors are to be detected, to remove the preexisting droplets by appropriate means such as particle filters as those mentioned hereunder and thus detect, after expansion, only droplets of condensible vapors.

The trace amounts of condensible vapors associated with the carrier gas such as nitrogen, oxygen, hydrogen, ..., are detected essentially by rapid cooling of the compressed carrier gas. Such rapid cooling is achieved by expanding the gas through a critical orifice.

The thermodynamics and fluid dynamics of critical orifices are well known and indicate that the temperature $T_2$ in the gas jet after the orifice by adiabatic expansion is:

$$T_2 = T_1(P_2/P_1)^{\frac{x-1}{x}} \text{ with } x = \frac{C_p}{C_v}$$

where
$T_1$ is the temperature of the gas before expansion
$P_1$ is the pressure of the gas before expansion
$P_2$ is the pressure of the gas after expansion
$C_p$ = specific heat capacity at constant pressure
$C_v$ = specific heat capacity at constant volume The actual temperature drop is considerably less, due to heat conduction from the critical orifice through the gas.

The rapid cooling leads to supersaturation of the condensible vapor. The supersaturation is defined as:

$$S = \frac{\text{vapor pressure before expansion}}{\text{saturation vapor pressure at temperature after expansion}}$$

Above a critical supersaturation Sc, for which values may be found in the literature for a variety of substances (see for example "Nucleation Theory by Zettlemoyer), the condensible vapor forms droplets by homogenous nucleation of the condensible vapor, i.e. without the presence of preexisting nuclei of condensation the filtering step provides a means for removing particles which could act as nuclei condensation. In this, the method according to the invention distinguishes itself from other methods requiring a preexisting mixture of vapor and particles.

The above described method implies that the gas is sufficiently compressed to allow for the necessary cooling expansion which is required to initiate homogeneous condensation. The method is thus especially suited for cylinder gases, which usually have an initial pressure of about 2500 psi: expansion to atmospheric pressure is thus more than sufficient to create the temperature drop for homogenous condensation of droplets.

The detection of trace amounts of vapor is made by detecting the droplets formed in the jet of expanded gas and, if so desired, making precise determinations of their concentrations and size distributions. The preferred method for detecting and concentration measurement is a condensation nuclei counter, of which several models are avalaible on the market. However other methods of droplet detection and sizing even of very small size are also well known, such as optical particle counters, electrical detectors, impaction methods or the like.

One of the advantages, among others, of the various methods of the invention is that very small amounts of condensible vapors can be detected, measured and/or removed, where "small" can mean levels as low as parts per trillion in concentration. However, this method is not limited to very low levels. The lowest detectable levels of the method according to the invention are given by three factors:

(i) the maximum pressure drop achievable without initiating condensation of the carrier gas itself, (ii) the amount of heat conducted into the expanding jet (cooling of the orifice can help offset a limited supply of pressure).

(iii) the thermodynamic properties of the vapor.

The method according to the invention makes it possible to quantify the concentration of condensible vapors in the carrier gas by the minimum pressure drop across the critical orifice necessary to cause the onset of droplet formation and the number of droplets per volume of gas so formed. This minimum pressure drop is determined for example, by comparing the droplet concentrations measured at various drops to a threshold concentration.

This method allows to provide relative values of concentration within a family of condensible vapors (such as useful during quality control in an industrial process). In that case, the method according to the invention is amenable to calibration. Absolute measures are possible where the exact physical and chemical properties of the vapor and the jet temperature are known.

Experiments have shown that sub-ppb levels of hydrocarbon contamination cause droplet formation of condensible vapors at pressure drops above about 20:1. This means that, according to the invention the detection, measurement and/or removal of such trace amounts of condensible vapors from compressed gases need a pressure drop of about 20:1 or more p.p.t. levels of contaminants. If the pressure of the compressed gas is too low to provide such pressure drop, the method according to the invention will first of all provide a step of compressing the gas to a pressure higher than that sufficient to cause such pressure drop.

The various embodiments of the method according to the invention make it possible to control and regulate industrial processes where the level of a condensible vapor is an important process parameter. In that case, the compressed gas is continuously discharged through the critical orifice with a pressure drop (and cooling of the said orifice, if necessary) sufficient to condense the vapors up to a predetermined purity level of said gas.

An example of such a regulation may be purification of gas with adsorption columns, wherein the switching from one adsorption column to the other is controlled by the concentration of condensible vapors measured (or detected) according to the method of the invention. As soon as said concentration is higher than a threshold value, there is a switching from one column to the other, and vice-versa (the regeneration of the column is realized during two successive switchings).

DETAILED DESCRIPTION OF THE INVENTION

These and furthers objects will be more clearly understood by reference to the following description of various embodiments of the invention, chosen for purpose of illustration only, along with the claims and the accompanying drawings wherein:

FIG. 1 schematically illustrates the method of the invention,

Figure 1:
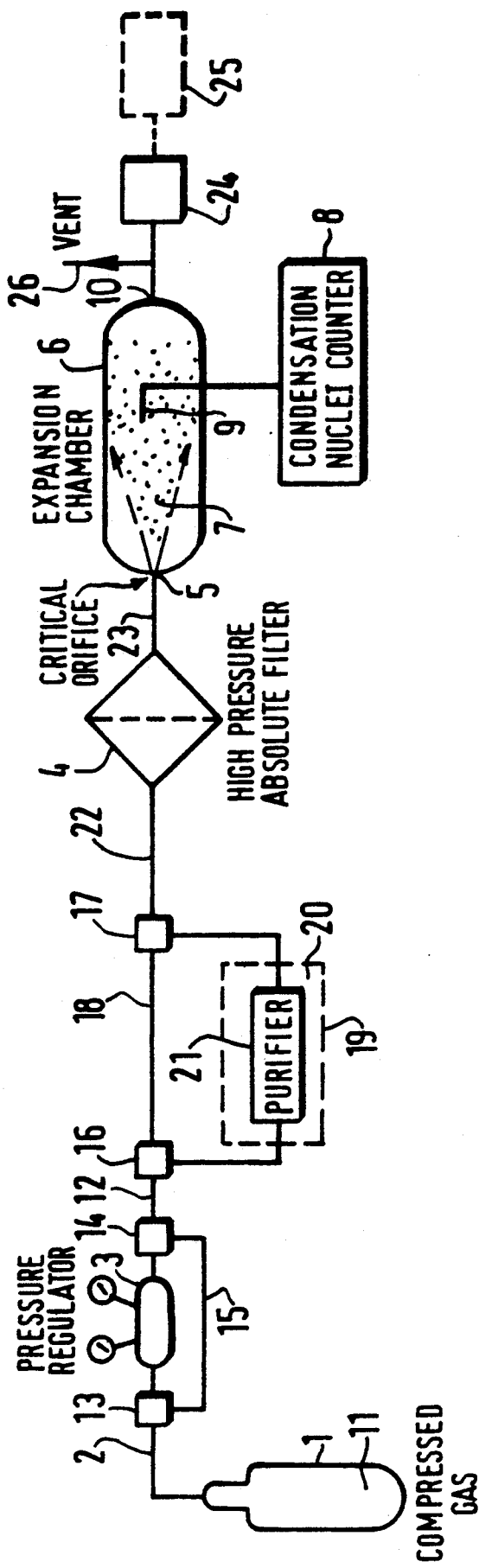

In FIG. 1, the high pressure compressed gas 11 from the cylinder 1 flows through the conduits 2 to a three way valve 13 and then either through the pressure regulator 3, or through the by-pass conduit 15, both outputs of which are connected to the three-way valve 14, then to the conduit 12 connected to the three-way valve 6. This valve 16 is, in turn connected to a by-pass conduit 18, on the one hand, and to purifying means 19 which may comprise a purifier 21 (molecular sieve or the like) surrounded, if necessary with cooling means 20 such as dry ice, liquid nitrogen or the like.

The output of the purifying means is connected to the three-way valve 17 being in turn connected to the high pressure absolute filter 4 via the conduit 22. The output of said filter is connected, through the conduit 23 to the critical orifice 5. The jet 7 of expanded gas and condensed vapors flows through the expansion chamber 6 and is exhausted by the output 10. The gas flowing from the output 10 may be either vented through the conduit 26 or sent to a filter 24 to remove the condensed vapors from said carrier gas. The purified gas can thus be sent to means to use it, such as a machine 25 to manufacture semi-conductor devices or any other means where it is necessary to use such high purity gas.

The condensed vapor droplets are detected and/or counted-by means of a condensation neclei counter 8 whose sensor 9 is placed in the flow of the expanded gas from the critical orifice.

The device disclosed on this FIG. 1 comprises all the means necessary for all the embodiments of the method according to the invention. However, all these means are not necessarily useful for all these embodiments as it will be explained thereafter.

FIRST EMBODIMENT OF THE INVENTION

Figure 2:
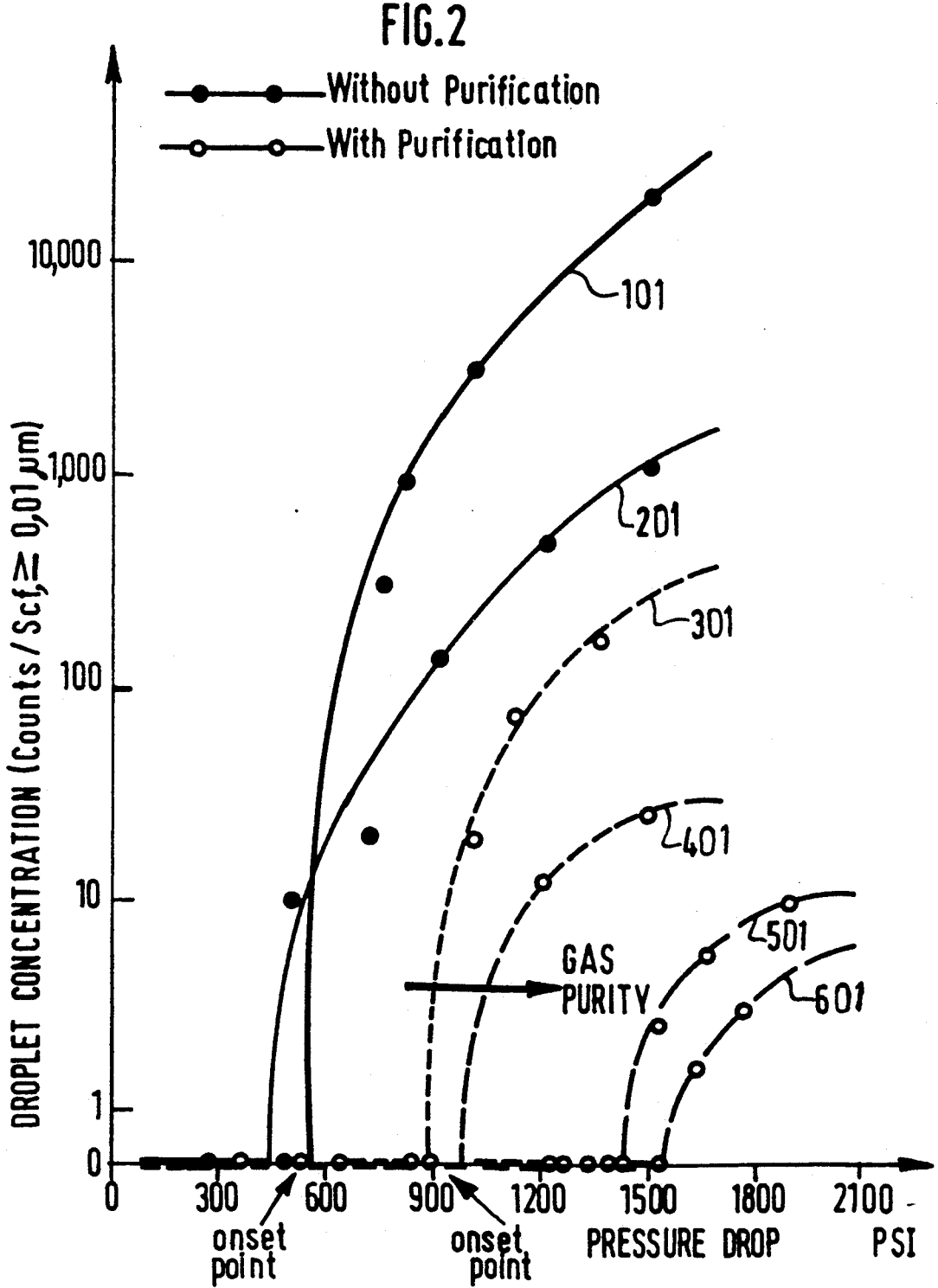
FIG. 2 shows various curves of the droplet concentration versus pressure.
Figure 3:
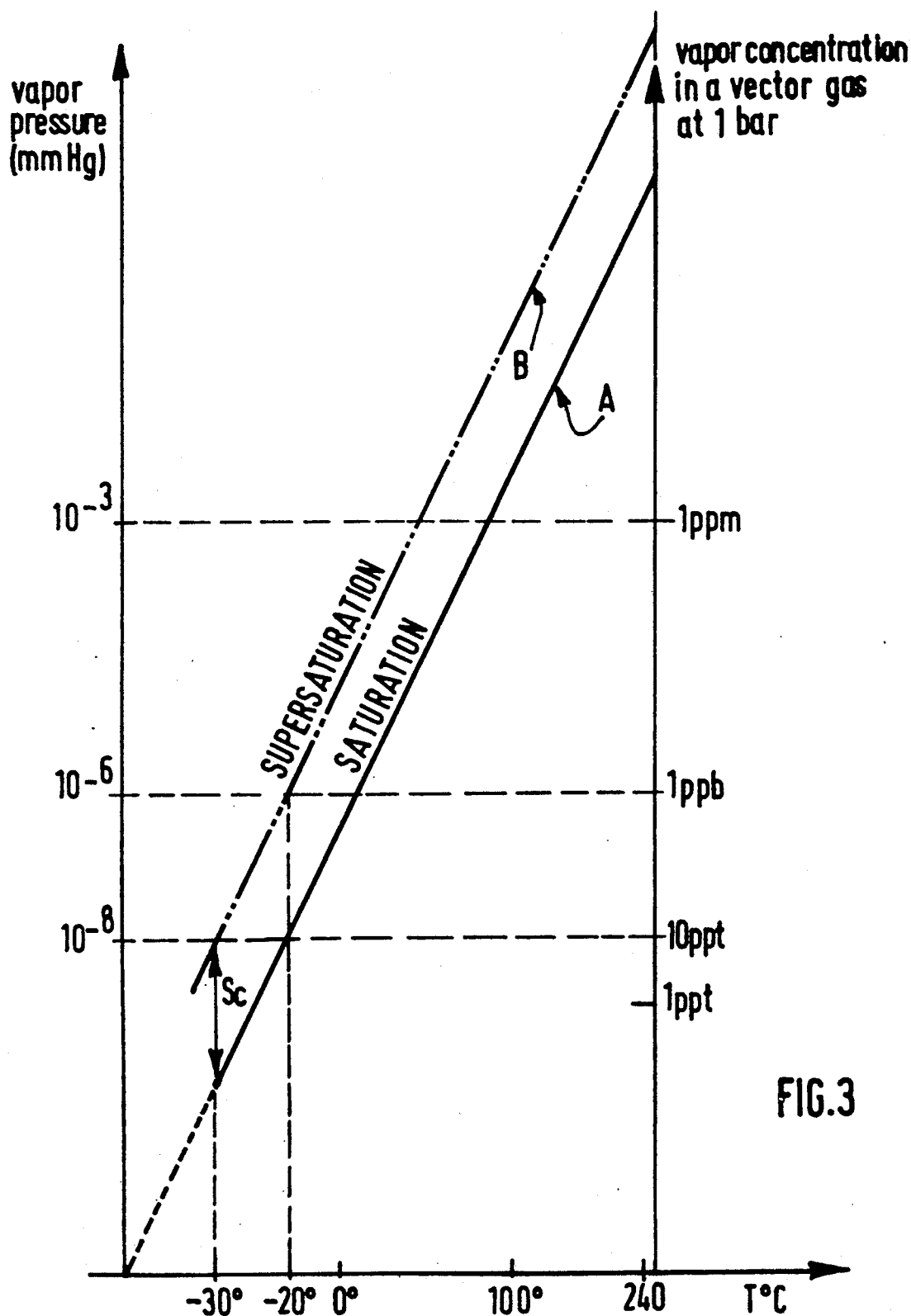
FIG. 3 illustrates an example of vapor pressure versus temperature for halocarbon oils.

In order to detect the presence of condensed vapors in the carrier gas, the compressed gas 11 is sent through conduits 2, 15 and 12 either through the conduit 18 (curves "without purification" on FIG. 2) or through the purifying means 19 (curves "with purification" on FIG. 2).

In both cases, it flows thereafter through the conduit 22, the filter 4, the conduit 23 and the critical orifice 5 where it is expanded in the chamber 6, then vented through the conduit 26. The droplets of vapors are detected by the sensor 9 of a particle detector such as a condensation nuclei counter 8. They may be counted (per unit of volume, or per time interval) if it is useful.

When this embodiment is carried out for purposes such as quality control of cylinders, the by-pass conduit 18 is used and the vapor droplets are detected for the given pressure drop between the cylinder pressure and the expansion chamber (generally, but not necessarily atmospheric pressure). The mere indication of the presence (or absence) of droplets is sufficient to decide whether the gas is "good" or "no good" for a specified application.

In some cases it may be useful for the compressed gas to be purified through means 19 to remove some vapors before detection and/or counting.

SECOND EMBODIMENT OF THE INVENTION

This embodiment is carried out as the first one, except that the number of droplets detected per volume unit of gas is counted and compared to a threshold value which could be different for different applications of the gas.

Depending on the gas, the possible vapors, the application of the gas, the pressure drop can be variable and the threshold value adapted.

The respective values of pressure drop and threshold are determined by comparison with a gas considered as acceptable for the application. Generally, the gas considered as acceptable for the application is analysed in order to draw the curves as those illustrated on FIG. 2, to determine the onset pressure drop point or area. Another way of defining the threshold and pressure drop values may be by comparison with the curve and/or values measured for the gas which has been purified before expansion as explained above.

THIRD EMBODIMENT OF THE INVENTION

In this embodiment, the pressure drop is varied either by using the pressure regulator 3, or by totally emptying the cylinder 1 and using the by-pass conduit 15. In both cases, either the purifying means 19 or the by-pass conduit 18 may be used.

Curves such as those of FIG. 2 represent various cases and show droplet concentration (counts of droplets having a diameter greater than or equal to 0.01 $\mu$m) versus pressure-drop.

Curves 101 and 201 represent the droplet concentration versus pressure drop for two different cylinders of nitrogen having a pressure of about 2500 psi at the beginning, without purification (by-pass conduit 18 is used). The onset points are respectively about 450 and 550 psi. Up to this pressure drop through the critical orifice, no particle is counted. Within a variation of about 50 psi of the pressure drop, about 10 droplets were counted, to reach 100 to 1000 droplets 50 psi higher. The onset point indicates a significant change in the slope of the curve and is thus a precise frontier.

Curves 301, 401 represent the same as curves 101, 201 but with the use of the purifying means 19 made of molecular sieve surrounded by dry ice. This purifying means 19 create a condensation of some vapors present in the gas which is thus purer than the same without purification.

The curves 301, 401 are thus similar to curves 101, 201, but with onset points corresponding respectively to pressure drops of about 890 and 990 psi, and droplet concentrations lower than that for the same gas, but without purification.

Curves 501, 601 represent the same as curve 301, 401, by using more efficient purifying means (the travel of the gas through the molecular sieve was longer, the temperature being about the same).

Onset points are thus about 1440 and 1560 psi for two different cylinders and the droplets concentrations are still lower than that of curves 301, 401.

FIG. 2 clearly indicates that as far as the purity of the gas increases, the onset pressure drop increases.

This third embodiment, according to which the onset point, among others, is determined, may have various applications. It can be used as such in order to give an indication of the purity of the gas.

It may also further comprise a step of determining the pressure drop at which the droplet concentration exceeds threshold value, giving a simple but quantified indication on the purity of the gas in a set of cylinders some of which have been taken to draw curves such as those of FIG. 2.

It may also, alternatively, comprise a further step of comparing the measured concentration of droplets for a specified pressure drop, to a threshold concentration of droplets, by a sole measure of said droplets concentration at said pressure drop for each cylinder of a set of the same cylinders or one cylinder among a set (for example, the droplet concentration for a pressure drop to atmospheric pressure. This control is thus "non destructive" for further cylinders. It is only "destructive" for the one used to draw the curve).

FOURTH EMBODIMENT OF THE INVENTION

In this embodiment, particularly useful to remove traces of condensible vapors up to a residual concentration of 1 ppt or less, no pressure regulator, no purifying means, no counting means such as 8 are necessary. The compressed gas is directly expanded to the low pressure, preferably atmospheric pressure, to have the greatest possible pressure drop and thus the highest concentration of vapour droplets in the jet 7. The droplets are removed through the filter 24 of a well known type and the highly purified gas may be used in means 25. Means (not represented on FIG. 1) may be necessary (around the expansion chamber and/or the critical orifice) to avoid reevaporation of the condensed droplets before they reach the filter 24.

In the various embodiments disclosed above, the high pressure absolute filter may be a ceramic filter such as sold by the PUREPON JAPAN Co. Ltd, made of three layers, a porous layer between two membrane type layers.

Filter means 24 to remove the condensed droplets are preferably filtration or absorption means generally used for the gas purification.

The various embodiments disclosed above in conjunction with FIGS. 1 and 2 indicate that even if particles are removed (by the filter 4) before expansion, droplets of condensible vapors may be formed: the invention is thus clearly distinct from the methods requiring preexisting particles to detect droplets.

FIG. 3 illustrates an example, for an HALOCARBON oil, of the way of using the various embodiments of the invention to detect, measure or remove vapors of such oil in a carrier gas.

Curve A (which is a straight line with the logarithmic scale chosen) represents the vapor pressure (in Hg mm) of said HALOCARBON oil having a viscosity of 1000 centipoise versus the temperature of the carrier gas (in Celsius degrees). On the Y- axis, but on the right of the figure, are indicated the vapor concentrations in a carrier gas at 1 bar (the "low" pressure when the compressed gas is expanded at atmospheric pressure). This curve is given by the manufacturer of such oils and is well-known. Curve B is the supersaturation vapor pressure of the same oil which is parallel to curve A at a distance equal to Sc. In that case, Sc is about 10. This curve B indicates the lowest limit of vapor concentration on the Y- axis- right versus the temperature of the gas, lowest limit at which homogeneous droplet condensation can still take place. It is clear from that curve B, which is only given as an example, that all the concentration of this oil of about 10 ppt or more may be detected if the gas is cooled (by expansion) at about −30° C. Concentrations of about 1 ppb or more may be detected if the gas is cooled at about −20° C.

Of course, lower temperature than −30° C. are easily achievable and thus sub p.p.t. concentrations may be detected.

We claim:

1. A method of detecting trace amounts of condensible vapors from a pressurized gas which may not contain condensation nuclei, comprising the steps of providing said compressed gas at a high pressure, filtering said compressed gas to remove particles present in said high pressure gas, expanding said compressed gas to a low pressure through a critical orifice means to form droplets of condensed vapors, and detecting the presence of droplets of condensed vapors in said low pressure gas.

2. A method according to claim 1, wherein said low pressure is atmospheric pressure.

3. A method according to claim 1, further comprising the step of purifying said compressed gas before expansion, in order to remove the condensed vapors.

4. A method according to claim 1 further comprising the step of cooling the critical orifice means.

5. A method of measuring the concentration of condesible vapors in a pressurized compressed gas which may not contain condensation nuclei, comprising the steps of providing said compressed gas at a high pressure, filtering said compressed gas to remove particles present in said high pressure gas, expanding said gas to a low pressure through a critical orifice means to form droplets of condensed vapors, measuring the droplet concentration of condensible vapors in the expanded gas, and comparing said measure to a threshold concentration.

6. A method according to claim 5, wherein said low pressure is atmospheric pressure.

7. A method according to claim 5, wherein the droplet concentration is measured by means of a condensation nuclei counter.

8. A method according to claim 5 further comprising the step of cooling the critical orifice means.

9. A method of measuring the concentration of condensible vapors in a pressurized compressed gas which may not contain condensation nuclei comprising the steps of providing said compressed gas at a high pressure, filtering said compressed gas to remove particles present in said high pressure gas, expanding said gas to a low pressure through a critical orifice means to form droplets of condensed vapors, varying the pressure drop across the critical orifice means and measuring the droplet concentration as a function of pressure drop.

10. A method according to claim 9, further comprising the step of comparing the measured droplet concentration with a threshold concentration of droplets.

11. A method according to claim 9, further comprising the step of determining the pressure drop at which the droplet concentration exceeds a threshold value.

12. A method of removing trace amounts of condensible vapors in a stored, pressurized compressed carrier gas which may not contain condensation nuclei, comprising the steps of providing said compressed gas at a high pressure, filtering said compressed gas to remove particles present therein, expanding said gas to a lower pressure through a critical orifice means, the pressure drop between said high and lower pressures being sufficient to cause the onset of droplets formation by said condensible vapors in the expanded carrier gas, maintaining the temperature of said expanded carrier gas at a value sufficient to avoid evaporation of the droplets, and capturing the droplets to remove the condensed vapors from said carrier gas.

13. A method according to claim 12, wherein the step of capturing the droplets comprises filtration.

14. A method according to claim 12, wherein the step of capturing the droplets comprises absorption.

15. A method according to claim 12, further comprising the step of storing the carrier gas free from said condensed vapors in a container.

16. A method according to claim 12, further comprising the step of using said carrier gas free from said condensed vapors immediately after the condensed vapors are removed therefrom.

17. A method according to claim 12, wherein said lower pressure is atmospheric pressure.

18. A method according to claim 12, further comprising the step of cooling the critical orifice means.

19. A method of measuring the concentration of condensible vapors in a gas compressed under high pressure, comprising the steps of providing said compressed gas at a high pressure, filtering said compressed gas to remove particles present in said high pressure gas, expanding said gas to a low pressure through a critical orifice to form droplets of condensed vapors, measuring the droplet concentration of condensible vapors in the expanded gas, and comparing said measure to a threshold concentration.

20. A method of removing trace amounts of condensible vapors in a compressed carrier gas stored at a high pressure, comprising the steps of providing a compressed gas at a high pressure, filtering said compressed gas to remove particles present therein, expanding said gas to a lower pressure through a critical orifice means, the pressure drop between said high and lower pressures being sufficient to cause the onset of droplet formation by said condensible vapors in the expanded carrier gas, maintaining the temperature of said expanded carrier gas at a value sufficient to avoid evaporation of the droplets, and capturing the droplets to remove the condensed vapors from said carrier gas.

* * * * *